United States Patent [19]

Fuchs

[11] 4,235,802
[45] Nov. 25, 1980

[54] PROPENIMIDATES

[75] Inventor: Julius J. Fuchs, Wilmington, Del.

[73] Assignee: E. I. Du Pont de Nemours and Company, Wilmington, Del.

[21] Appl. No.: 67,354

[22] Filed: Aug. 14, 1979

[51] Int. Cl.³ ............... C07C 125/08; C07C 119/18
[52] U.S. Cl. ......................... 260/453 RW; 544/247; 564/106
[58] Field of Search ............... 260/453 RW, 551 C

[56] References Cited

U.S. PATENT DOCUMENTS

| | | | |
|---|---|---|---|
| 2,697,727 | 12/1954 | Kaiser et al. ............ | 260/551 C |
| 3,225,077 | 12/1965 | Schaefer et al. ......... | 260/453 RW |
| 3,439,031 | 7/1969 | Blanchard ............... | 260/551 C |
| 3,658,901 | 7/1972 | Timmons et al. ......... | 260/453 RW |
| 3,849,465 | 11/1974 | Marsh .................... | 260/453 RW |
| 4,108,883 | 8/1978 | Panzer et al. ........... | 260/453 RW |

FOREIGN PATENT DOCUMENTS 46-41293  12/1971  Japan ............... 260/551 C

Primary Examiner—Thomas A. Waltz

[57] ABSTRACT

Propenimidates are provided having the formula:

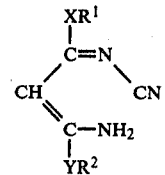

wherein
X and Y are independently O or S; and
R¹ and R² are independently $C_1-C_4$ alkyl, $(CH_2)_nOR^3$ where R³ is $C_1-C_4$ alkyl and n is 1 or 2, $CH_2CH_2Cl$, or $CH_2CF_3$, provided that when R¹ or R² is $CH_2CH_2Cl$ or $CH_2CF_3$, then the respective X or Y is O.

Preferred propenimidates have X and Y as O and R¹ and R² as methyl or ethyl.

The propenimidates are made by preparing a monohydrohalide salt from a dihydrohalide salt of the formula:

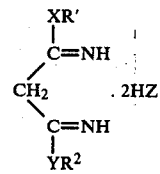

and then contacting the monohydrohalide salt with cyanamide.

The propenimidates upon heating ring close to pyrimidines which are useful in preparing herbicidal compounds.

4 Claims, No Drawings

PROPENIMIDATES

DESCRIPTION OF THE INVENTION

1. Field of Invention

This invention relates to propenimidates, processes for their preparation and processes to prepare pyrimidines therefrom.

2. Background of the Invention

Coassigned application Ser. No. 840,389, filed Oct. 6, 1977, in the name of George Levitt, now U.S. Pat. No. 4,169,719 describes herbicidal sulfonamides prepared by reacting an appropriate 2-amino pyrimidine with an appropriately substituted sulfonyl isocyanate or isothiocyanate. The described sulfonamides are active herbicides and are especially useful in controlling nutsedge in crops such as cotton, corn, rice and wheat.

The development of an attractive process for preparing the above described sulfonamides by necessity involves inexpensive, easy to carry out processes for preparing the pyrimidine and isocyanate or isothiocyanate intermediates. The pyrimidine intermediate has been difficult to prepare due to hazards associated with raw materials and waste streams. Thus, any simplification in the preparation of the pyrimidine intermediate is desirable.

DETAILED DESCRIPTION OF THE INVENTION

According to the present invention there is provided a compound of the formula:

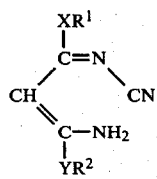

wherein

X and Y are independently O or S; and $R^1$ and $R^2$ are independently $C_1$–$C_4$ alkyl, $(CH_2)_nOR^3$ where $R^3$ is $C_1$–$C_4$ alkyl and n is 1 or 2, $CH_2CH_2Cl$ or $CH_2CF_3$, provided that when $R^1$ and $R^2$ is $CH_2CH_2Cl$ or $CH_2CF_3$, then the respective X or Y is O.

In the compounds of the invention, X and Y are preferably both O or both S, most preferably O; and $R^1$ and $R^2$ are preferably independently methyl or ethyl, most preferably both are methyl. Thus, the preferred compound of the invention is methyl 3-amino-3-methoxy-N-cyano-2-propenimidate.

There is also provided a process for preparing the above-described compound which comprises:

(a) contacting a dihydrohalide salt of the formula:

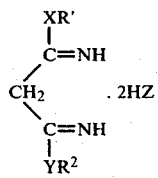

wherein X, Y, $R^1$ and $R^2$ are as defined above and Z is F, Cl or Br, in an inert liquid medium with one equivalent weight of a base at a pH no higher than about 7, to produce a monohydrohalide salt; and, (b) contacting the monohydrohalide salt with cyanamide.

Further provided is a process for preparing a compound of the formula:

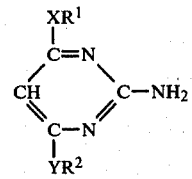

wherein X, Y, $R^1$ and $R^2$ are as defined above, which comprises heating the compound according to the present invention at a temperature sufficient to ring close.

The process of the invention for preparing compounds of the invention (I) and their subsequent conversion to pyrimidines (IV) useful as herbicide intermediates is exemplified by the following reactions:

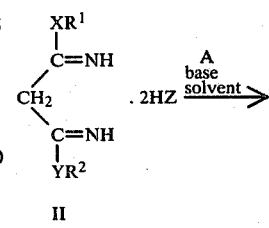

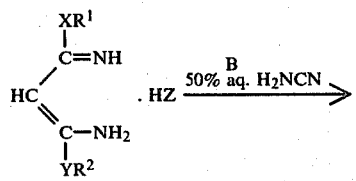

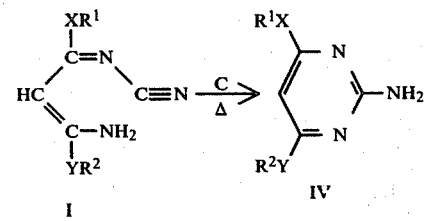

where Z is F, Cl, or Br and X, Y, $R^1$ and $R^2$ are as defined previously.

In the first step of the process, reaction A, a dihydrohalide salt, preferably a dihydrochloride salt, of a bismalonimidate of formula II is contacted with one equivalent weight of a base at a pH no higher than about 7 in an inert liquid medium to produce a monohydrohalide salt (III). The base is preferably an alkali metal (preferably sodium) bicarbonate, carbonate, hydroxide or methoxide, pyridine or triethylamine (or any other tertiary amine base). Sodium carbonate, sodium bicarbonate or sodium hydroxide are the most preferred bases usually used as their aqueous solutions. The liquid medium used to suspend or dissolve the reactants can be any liquid inert to the reaction. Typical liquids are halogenated compounds such as $CH_2Cl_2$, or $CHCl_3$, ethers such as diethylether or dioxane, esters such as methylacetate or ethylacetate, alcohols such as methanol or ethanol, or hydrocarbons such as benzene, toluene, hexane or cyclohexane. The pH of the reaction mixture is preferably maintained in the range of about 5-7. Temperature of the reaction is preferably in the range of about −10° C. to about 20° C.

Reaction A can preferably be carried out by any one of the following procedures:

(1) to a suspension of (II) in a liquid in which the synthesis of (II) has been performed, is added at −10° to 20° C. enough base to neutralize any excess free hydrohalide (chloride) acid which may still be present from the synthesis of (II), plus one equivalent of base to convert (II) to (III);

(2) solid (II) is suspended in any one of the described liquid mediums and then contacted with one equivalent of base at −10° to 20° 1 C.;

(3) solid (II) is added to one equivalent of one of the preferred aqueous bases, i.e., $Na_2CO_3$, $NaHCO_3$ or NaOH, at −10° to 20° C.; or (4) a suspension of (II) in one of the described liquid mediums is added simultaneously with one equivalent of an aqueous base to ice water, maintaining a pH of 5-7 by regulating the addition rate of either stream. The preferred procedure is either (3) or (4).

A compound of (II), dimethyl 1,3-propanediimidate dihydrochloride (X and Y=O; $R^1$ and $R^2$=methyl), is known in the art. S. M. McElvain and J. P. Schroeder, JACS 71, 40(1949); B. Harsteen, German Offenlegungsschrift 2,426,913, Dec. 11, 1975. Other compounds of (II) can be made by the procedures described.

In reaction B, the monohydrohalide salt compound of formula (III) is contacted with cyanamide ($H_2NCN$), preferably 50 percent by weight aqueous cyanamide. The reaction is preferably carried out in a solvent such as water, a lower alcohol or mixtures thereof, preferably water. The reaction can also be carried out in the presence of a water-immiscible solvent such as methylene chloride to extract compound (I) as it is formed. Temperature of reaction is usually in the range of about 20°-75° C., preferably about 25°-50° C., for a time sufficient to give compound (I), i.e., 15 minutes to 5 hours, normally about 1 to 3 hours.

Reaction B can be carried out by one of the following procedures:

(1) to the reaction mass obtained in reaction A (1), (2) or (4) is added an equivalent or a slight excess (about 10%) of cyanamide, preferably as 50% aqueous cyanamide, and the reaction mass stirred until the reaction is completed (up to 5 hours at 20° C. to 15 minutes at 75° C.). Water is then added to dissolve any salts present. Any undissolved product (I) is then isolated by filtration, then the aqueous phase is separated from the organic phase and (I) isolated from the organic phase by evaporation of the solvent; or (2) to the solution obtained in reaction A (3) is added an equivalent or a slight excess (about 10%) of aqueous cyanamide and the solution warmed to room temperature where it is held for about 2 hours. Solid product (I), which precipitates during this time, is then isolated by filtration.

As shown in reaction C, compounds of the invention (I) can be caused to undergo ring closure to the herbicide intermediates (IV) by heating. Preferably, compound (I) is dissolved or suspended in a suitable inert liquid medium such as water, methanol, toluene or xylene and maintained at a temperature in the range of about 0° to about 200° C., preferably about 50°-150° C., until the rearrangement is complete. Alternatively, ring closure can be accomplished by heating the neat compound of formula (I) to a temperature above its melting point for a suitable period of time.

Reaction C is exemplified by one of the following procedures:

(1) a solution or suspension of (I) in an inert liquid medium is heated to 65°-110° C. until rearrangement is complete (several hours at 65° C. to about 60 minutes at 110° C.); then the solution or suspension is cooled and (IV) isolated by filtration or evaporation of the solvent;

(2) a compound of formula (I) is heated neat to its melting point, e.g., when X and Y=O and $R^1$ and $R^2$=methyl, heating to about 130° C. will give ring closure in less than one minute. The ring closure reaction of either procedure is highly exothermic and can lead to boiling of the liquid or a considerable rise in temperature of the melt when (I) is heated neat. Reaction C (1) can easily be carried out in the reaction mass obtained from reaction B, without isolation of product (I), by heating and distilling out any organic solvent present, either as neat solvent or as an azeotrope with water. In the latter case, the aqueous solution of (I) is maintained at temperature to complete the ring closure. After cooling, (IV) is isolated by filtration.

The pyrimidine of formula (IV) is reacted with a substituted sulfonyl isocyanate or isothiocyanate as described in the aforesaid U.S. Ser. No. 840,389 to produce a herbicidal sulfonamide. This patent is hereby incorporated by reference.

By using the procedures described, the following compounds of formula (I) can be prepared:

| X | Y | $R^1$ | $R^2$ |
|---|---|---|---|
| O | O | $CH_3$ | $CH_3$ |
| O | O | $CH_3$ | $CH_2CH_2CH_2CH_3$ |
| O | O | $CH_3$ | $CHCH_3$<br>\|<br>$CH_3$ |
| O | O | $CH_3$ | $CH_2CH_2OCH_3$ |
| O | O | $CH_3$ | $CH_2OCH_2CH_2CH_2CH_3$ |
| O | O | $CH_3$ | $CH_2CH_2Cl$ |
| O | O | $CH_3$ | $CH_2CF_3$ |
| O | S | $CH_3$ | $CH_3$ |
| O | S | $CH_3$ | $-CHCH_2CH_3$<br>\|<br>$CH_3$ |
| S | S | $CH_3$ | $CH_3$ |
| S | S | $CH_3$ | $CH_2CH_3$ |
| S | S | $CH_3$ | $-CH_2CHCH_3$<br>\|<br>$CH_3$ |
| S | S | $CH_3$ | $CH_2OCH-CH_3$<br>\|<br>$CH_3$ |
| S | S | $CH_3$ | $CH_2CH_2OCH_3$ |
| O | O | $CHCH_3$<br>\|<br>$CH_3$ | $CHCH_3$<br>\|<br>$CH_3$ |
| O | O | $CH_2CH_3$ | $CH_2CH_3$ |
| S | S | $CH_2CH_3$ | $CH_2CH_3$ |
| O | S | $CH_2CH_3$ | $CH_2CH_3$ |
| O | O | $CH_3$ | $CH_2CH_3$ |
| O | O | $CH_3$ | $-CH_2CHCH_3$<br>\|<br>$CH_3$ |
| O | O | $CH_3$ | $-CHCH_2CH_3$<br>\|<br>$CH_3$ |
| O | O | $CH_3$ | $CH_2OCHCH_3$<br>\|<br>$CH_3$ |
| O | O | $CH_3$ | $CH_2OCH_2CH_3$ |

| X | Y | R¹ | R² |
|---|---|---|---|
| O | O | CH₃ | CH₂OCHCH₂CH₃<br>\|<br>CH₃ |
| O | O | CH₃ | CH₂CH₂OCH₂CH₃ |
| O | O | CH₃ | CH₂CH₂OCHCH₃<br>\|<br>CH₃ |

The invention can be further understood by the following examples in which parts and percentages are by weight unless otherwise indicated.

EXAMPLE 1

(a) A suspension of 101.5 g of dimethyl 1,3-propanediimidate dihydrochloride in 200 ml of methanol was treated at 0° C. with 216 g of a 25% solution of sodium methylate in methanol until a pH of 6 was obtained. Solid NaCl, which had precipitated, was then removed by filtration and the filtrate evaporated under vacuum until a viscous solution of the monohydrochloride salt in methanol remained. This solution was then triturated with acetone to precipitate the monohydrochloride salt, which was recovered by filtration. Melting point 91°–93° C.; 21.3% chloride content; yield 90%.

(b) The monohydrochloride salt from above (16.7 g) was heated with 10 g of 50% aqueous cyanamide, 10 ml of water and 300 ml of $CH_2Cl_2$ for one hour at 40° C. The organic phase was then separated, dried and the solvent removed under vacuum to give 12.8 g of methyl 3-amino-3-methoxy-N-cyano-2-propenimidate mp 128°–130° C.

EXAMPLE 2

To a suspension of 42 g NaHCO₃ in 400 ml of water at 0° C. was added, in small portions, at a pH greater than 5, 101.5 g of diemthyl 1,3-propanediimidate dihydrochloride. To the resulting solution was added 45 parts of 50% aqueous cyanamide and the solution warmed to room temperature where it was held for 2 hours. Solid product, methyl 3-amino-3-methoxy-N-cyano-2-propenimidate, precipitated during this time, which was then removed by filtration, washed with water and dried. mp 128°–129° C., after recrystallization from methanol, mp 131°–132° C. A small second crop of product was isolated from the aqueous filtrate by extraction with $CH_2Cl_2$ and evaporation of solvent.

EXAMPLE 3

One gram of recrystallized product from Example 2 was heated in a test tube with the aid of an oil bath to its melting point of 131° C., at which point a sudden release of energy raised the temperature of the melt to 190° C. The melt was then cooled and solidified. The resulting product melted at 94°–96° C. and its IR spectrum was identical with pure 2-amino-4,6-dimethoxypyrimidine.

EXAMPLE 4

A suspension of 5 g of recrystallized product from Example 2 in toluene was refluxed for 60 minutes. The toluene was evaporated from the resulting solution to give 2-amino-4,6-dimethoxypyrimidine in quantitative yield, mp 94°–96° C.

EXAMPLE 5

A suspension of 101.5 g of dimethyl 1,3-propanediimidate dihydrochloride in 2 liters of $CH_2Cl_2$ was gradually added together with 50% NaOH to 400 ml of water contained in a reactor, maintained at 0° to −5° C., at rates such that the pH of the aqueous solution was maintained between 5–7. Then, 45 g of 50% aqueous cyanamide was added and the resulting two-phase reaction mass refluxed at 40° C. for one hour. After phase separation, the $CH_2Cl_2$ phase was dried by distilling $CH_2Cl_2$ and azeotroping the water. The resulting solution of methyl 3-amino-3-methoxy-N-cyano-2-propenimidate in $CH_2Cl_2$ was gradually fed to xylene maintaining the temperature at 100°–130° C. while flashing off and condensing $CH_2Cl_2$. After all of the solution was fed, the solution was held at temperature for 15 minutes and then filtered. There was obtained 2-amino-4,6-dimethoxypyrimidine, mp 94°–96° C.

What is claimed is:

1. A compound of the formula:

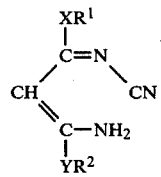

wherein

X and Y are independently O or S; and

R¹ and R² are independently $C_1$–$C_4$ alkyl, $(CH_2)_nOR_3$ where R³ is $C_1$–$C_4$ alkyl and n is 1 or 2, $CH_2CH_2Cl$ or $CH_2CF_3$, provided that when R¹ or R² is $CH_2CH_2Cl$ or $CH_2CF_3$, then the respective X or Y is O.

2. A compound of claim 1 wherein X and Y are both O or both S.

3. A compound of claim 2 wherein R¹ and R² are independently methyl or ethyl.

4. A compound of claim 1 wherein X and Y are O and R¹ and R² are methyl.

* * * * *